United States Patent [19]

Sakurai et al.

[11] Patent Number: 4,519,799
[45] Date of Patent: May 28, 1985

[54] SANITARY NAPKIN

[75] Inventors: Akira Sakurai, Utsunomiya; Hiroshi Mizutani, Yachiyo, both of Japan

[73] Assignee: Kao Corporation, Tokyo, Japan

[21] Appl. No.: 465,692

[22] Filed: Feb. 10, 1983

[30] Foreign Application Priority Data

Feb. 19, 1982 [JP] Japan ................................ 57-25671

[51] Int. Cl.³ ............................................. A61F 13/16
[52] U.S. Cl. .................................................... 604/366
[58] Field of Search ............... 604/366, 367, 370, 374, 604/378, 379

[56] References Cited

U.S. PATENT DOCUMENTS 4,417,893 11/1983 Mizutani et al. .................... 604/366

Primary Examiner—John D. Yasko
Attorney, Agent, or Firm—Flynn, Thiel, Boutell & Tanis

[57] ABSTRACT

The invention relates to a sanitary napkin having high liquid absortivity and excellent touch to the skin. The napkin is comprised of an internal absorbent medium and a covering fabric. The covering fabric has an integrated two layer structure wherein each layer is made from different compositions of heat fusible and hydrophobic fibers.

10 Claims, 1 Drawing Figure

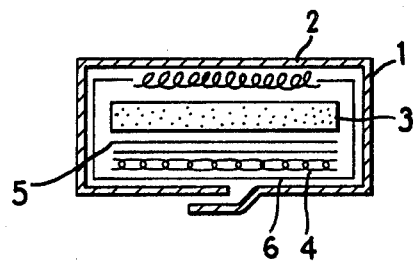

SANITARY NAPKIN

This invention relates to a sanitary napkin having high liquid absorptivity and excellent touch to the skin.

The conventional sanitary napkins have been comprised of an absorbent medium composed of fluff pulp, absorbent paper or the like, a leakproof layer disposed below and on the sides of said absorbent medium and a covering layer of nonwoven fabric.

As the nonwoven fabric forming the covering layer of such known sanitary napkins, it has been conventional to use wet-process or dry-process nonwoven fabrics. However, wet-process nonwoven fabrics have a dense texture and exhibit water repellency because they contain hydrophobic fibers or binder mixed therein, so that they are not completely satisfactory in the property of absorption of blood. In the case of dry-process nonwoven fabrics, because they use a binder for fixing the hydrophilic fibers, they also exhibit water repellency which makes them not completely satisfactory for absorption of blood, as in the case of wet-process nonwoven fabrics.

For these reasons, in practical use of such conventional sanitary napkins, if the blood effuses from the body at a high rate, it tends to flow along the upper surface of the napkin before it is absorbed into the interior thereof, thereby causing leakage of the blood beyond the lateral edges of the sanitary napkin.

Also, in certain cases, part of the effluent blood, after once being absorbed in the napkin, may be forced out of the napkin through the surface layer thereof because of the pressure of the user's body weight thereon, thereby causing wetting of the user's skin and detracting from the comfort and sense of security that are desired when sanitary napkins are worn. In order to minimize such "return" or "wet-back" of blood, attempts have been made to render the nonwoven fabric of the covering layer water-repellent. For instance, it has been proposed to use hydrophobic synthetic fibers as part of the component fibers of the nonwoven fabric. This can considerably ameliorate the blood returning or seeping phenomenon, but because of the water repellency, the absorptivity of the napkin for the effluent blood is seriously reduced and the napkin cannot be safe against edgewise leakage of blood.

As discussed above, it is desired that the sanitary napkin can satisfy both requirements, namely, it must be capable of quickly absorbing the effluent blood and it must also be capable of preventing the absorbed blood from being forced out under the pressure of the user's body weight. Various improvements, such as application of various kinds of liquid-absorptive polymers as the absorbent medium, have been reported and have been used in practice in commercially available sanitary napkins, but there is not yet available a sanitary napkin which can well satisfy both of the requirements of quick absorption (safety against edgewise leakage) and inhibition of "return" of previously absorbed liquid.

The present inventors have pursued further studies in search of a sanitary napkin which can simultaneously satisfy both of the aforementioned requirements, which involve contradictory considerations, and, as a result, have discovered the present invention.

The present invention provides a sanitary napkin in which the covering layer is composed of (1) 30 to 80% by weight of heat-fusible fiber which is fusible at 90° to 140° C. and (2) 70 to 20% by weight of hydrophobic fiber which is not fusible at a temperature below 140° C., said covering layer being provided on at least the surface portion of the sanitary napkin that touches the user's skin, said covering layer being specifically designed to have a thickness of 0.5 to 1.2 mm under a load of 1 g/cm² and a thickness of 0.2 to 0.6 mm under a load of 5 g/cm² and consisting essentially of a first layer or stratum which touches the user's skin and a second layer or stratum disposed inside said first layer, wherein the ratio by weight of said heat-fusible fiber to said hydrophobic fiber is from 50/50 to 100/0 in the first layer and is from 20/80 to 60/40 in the second layer.

Regarding the heat-fusible fiber used in this invention, it is basically possible to employ any suitable type of fiber which is partly or entirely fused when it is exposed to a temperature of 90° to 140° C. so as to exhibit adhesiveness, but usually a polyethylene/polypropylene composite fiber, a low-melting polyester/polypropylene composite fiber or the like is preferred.

As the hydrophobic fiber which is not fused at a temperature below 140° C., there can be used conventional synthetic fibers, preferably olefin fibers, such as polyethylene or polypropylene fiber, polyester fibers, polyamide fibers, or acrylonitrile fibers. Among them, polyolefin fibers are most preferred because of their low cost.

As for the size of the fiber used in this invention, the heat-fusible fiber can have a fineness within the range of 1.5 to 6 deniers, but a fiber fineness in the range of about 1.5 to 3 deniers is preferred, taking into consideration the fact that the heat-fusible fiber is used as the principal component of the first layer (on the side of the napkin which touches the user's skin), that is, at a location where importance is attached to the feel or touch of the first layer.

As regards the hydrophobic fiber, its fineness is preferably within the range of 1.5 to 6 deniers, more preferably, 1.5 to 3 deniers, for the same reason (good touch or feel).

The web structure of the covering fabric is preferably such that the second layer is rather weakly bonded to the first layer. As for the thickness of the nonwoven covering fabric, it is suitable for the puroses of this invention to use a nonwoven covering fabric which will have a thickness of 0.2 to 0.6 mm under a load of 5 g/cm² and a thickness of 0.5 to 1.2 mm under a load of 1 g/cm².

A nonwoven covering fabric having a thickness of less than 0.2 mm under a load of 5 g/cm² and a thickness of less than 0.5 mm under a load of 1 g/cm² is too thin and the layers are bonded to each other in a dense state which is devoid of the desired sense of voluminousness or fullness, so that such a fabric is poor in feel, touch and softness and also provides a greater possibility of return or seepage of the blood after it has been once absorbed in the napkin.

Nonwoven covering fabrics having a thickness of greater than 0.6 mm under a load of 5 g/cm² and a thickness of greater than 1.2 mm under a load of 1 g/cm² are also undesirable for the following reasons.

Firstly, when a nonwoven fabric retains a thickness of greater than 0.6 mm under a load of 5 g/cm², such a nonwoven fabric is bound to be very hard and naturally, such a nonwoven fabric will have a thickness of greater than 0.5 mm when placed under a load of 1 g/cm².

Secondly, when such a fabric has a thickness exceeding 1.2 mm under a load of 1 g/cm², such a fabric is not much different from a mere fiber aggregate in terms of texture, and such a fabric will be unable to withstand physical friction in actual use.

The nonwoven covering fabric used in this invention, which has a thickness of 0.2 to 0.6 mm under a load of 5 g/cm$^2$ and a thickness of 0.5 to 1.2 mm under a load of 1 g/cm$^2$, is excellent in feel, particularly in touch and softness, owing, for one thing, to weak bonding of the second layer to the first layer. This can be derived from the difference of thickness under the two different loads (1 g/cm$^2$ and 5 g/cm$^2$). Also, when the blood absorbed by the absorbent medium in the napkin is urged to exude to the surface of the napkin through said nonwoven fabric under a certain pressure, such blood will not be permitted to flow out directly to the surface owing to the thickness of the covering fabric that is retained under the load of 5 g/cm$^2$, thus ensuring an improvement of the napkin of this invention in the properties of reduced tackiness and improved comfort during use.

Also, the covering layer of the sanitary napkin of this invention has an additional advantage that fluffing, due to physical friction in use, is minimized because of the fast and secure bonding of the fibers of the outermost layer (first layer) which is principally composed of heat-fusible fibers (50–100% by weight).

However, because the first layer is principally composed of heat-fusible fibers, the surface of the covering fabric of the sanitary napkin of this invention has a tendency to become hard and hence worsened in comfort when its basis weight (weight per m$^2$ of surface area) increases. Therefore, it is desirable that the first layer has a basis weight of from 5 to 15 g/m$^2$. As for the second layer, because the proportion of heat-fusible fibers in this layer is as low as 20 to 60% by weight and also because the fibers of this layer are rather weakly bonded, it is desirable that the second layer has a basis weight of 8 to 25 g/m$^2$.

The nonwoven covering fabric of the sanitary napkin according to this invention can be produced, for example, in the following way.

First, a web of a fiber aggregate which serves as the first layer (outermost layer) is formed by using a conventional textile fiber carding process and then a web of another fiber aggregate, which serves as the second layer and wherein the fibers are arranged in partially random and partially oriented configuration, is overlaid on said first layer with a net-like support therebeneath, and then hot air is flowed through the web from the second layer side toward the first layer side by a hot-air-passing-type of heat-treating machine whereby to bond both layers together. The hot air has a sufficiently high temperature to cause fusion of the surfaces of the heat-fusible fibers, but not to fuse the hydrophobic fibers. The temperature and duration of the heating are controlled so that the heat-fusible fibers are not melted completely, but rather, they retain their basic structural integrity and they are bonded together and to the hydrophobic fibers at the locations where the fibers touch each other.

The sanitary napkin of this invention is not subject to any specific restrictions on the construction and configuration of its absorbent medium.

BRIEF DESCRIPTION OF THE DRAWING

The drawing is a cross-sectional view of a sanitary napkin according to the invention.

The drawing illustrates a typical embodiment of the absorbent medium which is made of rayon staple fiber or cotton fiber 2, fluff pulp 3, a polymer absorbent layer 4 and an absorbent paper 5. However, the absorbent medium can be composed of fluff pulp or absorbent paper alone. The bottom and sides of the absorbent medium are covered by a waterproof paper or film 6. The sanitary napkin is covered by a nonwoven fabric 1 as described above. Although, in the illustrated embodiment of this invention, the entire absorbent medium is covered by the covering fabric 1, it is also possible to apply the covering fabric 1 of this invention so that it covers only the surface of the absorbent medium while the other surfaces are covered with a so-called leak-proof layer.

The invention will be described in further detail hereinbelow by reference to specific illustrative examples thereof.

EXAMPLE 1

Sanitary napkins having a size of 75×195 mm were made by using a nonwoven covering fabric 1, rayon staple fibers 2 (0.3 g), absorbent paper 5 (0.6 g), fluff pulp 3 (2.5 g), polylaminated waterproof paper 6 (0.6 g) and a polymer absorbent layer 4 (formed by sandwiching a highly water absorptive polymer between absorbent paper sheets; water-absorptive polymer: 0.3 g, absorbent paper: 0.6 g) as shown in the drawing. As the covering fabric 1, there were used various nonwoven fabrics composed of various combinations of first and second layers formed by using commercially available fiber materials as set forth in Table 1. The produced sanitary napkins were subjected to tests for determining the surface flow of liquid and liquid seepage (wet-back) (the amount of the liquid which seeped or returned to the outside of the napkin) under pressure. The results are shown in Table 1.

The distance (mm) of the surface flow of liquid, the wet-back amount (g) and napkin thickness (mm) (under loads) were measured by the following methods.

Surface flow:

Fibrinogen-free horse blood was dropped, from a distance of 1 cm above the sample, onto the upper surface of the sample which sample was inclined at an angle of 45° to the horizontal. The distance through which the blood flowed on the upper surface of the nonwoven fabric from the location at which the blood was dropped onto the sample to the location at which the blood was completely absorbed was measured. The shorter the distance, the greater is the absorbing rate, which signifies a reduced amount of or no edgewise leakage of the blood.

Wet-back:

10 cc of fibrinogen-free horse blood was absorbed in each sample and, after the passing of a given period of time, pressure was applied to the sample. There was measured the amount of the blood which seeped, that is, returned to the outside of the sample napkin from the inside thereof through the nonwoven fabric. The smaller the seepage, the less will be the tackiness of the napkin surface and hence the better will be the comfort during use.

Thickness:

10 sheets of each sample napkin cut to a suitable size were placed one upon another. The thickness of the stack was measured when loads of 1 g/cm$^2$ and 5 g/cm$^2$ were applied, respectively. The thickness of each sheet was calculated from the observed results.

TABLE 1

| First layer | | | Second layer | | | Basis weight | Proportion of heat-fusible fiber | Thickness 1 g/cm².hr | 5 g/cm².hr | Surface flow | Wet-back |
|---|---|---|---|---|---|---|---|---|---|---|---|
| Heat-fusible fiber | Hydrophobic fiber | Basis weight | Heat-fusible fiber | Hydrophobic fiber | Basis weight | | | | | | |
| ES*¹ 1.5d 100% | — | 8 g/m² | ES 3d 20% | PP 2d 80% | 12 g/m² | 20 g/m² | 52% | 0.63 mm | 0.36 mm | 24 mm | 1.8 g |
| ES 1.5d 100% | — | 8 | ES 3d 40% | PP 2d 60% | 12 | 20 | 64 | 0.60 | 0.36 | 26 | 1.7 |
| ES 1.5d 100% | — | 8 | ES 3d 60% | PP 2d 40% | 12 | 20 | 76 | 0.59 | 0.30 | 28 | 1.7 |
| ES 1.5d 70% | PP*³ 2d 30% | 8 | ES 3d 20% | PP 2d 80% | 12 | 20 | 40 | 0.68 | 0.41 | 26 | 1.4 |
| ES 1.5d 50% | PP 2d 50% | 8 | ES 3d 20% | PP 2d 80% | 12 | 20 | 32 | 0.74 | 0.41 | 24 | 1.5 |
| ES 1.5d 100% | — | 5 | ES 3d 40% | PP 2d 60% | 8 | 13 | 63 | 0.51 | 0.27 | 22 | 2.2 |
| ES 1.5d 100% | — | 10 | ES 3d 40% | PP 2d 60% | 18 | 28 | 61 | 0.96 | 0.51 | 24 | 1.8 |
| ES 1.5d 100% | — | 15 g/m² | ES 3d 40% | PP 2d 60% | 25 g/m² | 40 g/m² | 63% | 0.15 mm | 0.58 mm | 27 mm | 1.0 g |
| ES 1.5d 70% | PP 2d 30% | 8 | ES 3d 20% | PP 2d 80% | 12 | 20 | 40 | 0.52 | 0.23 | 26 | 1.4 |
| ES 1.5d 70% | PP 2d 30% | 8 | ES 3d 20% | PP 2d 80% | 12 | 20 | 40 | 0.72 | 0.55 | 27 | 1.6 |
| ES 3d 70% | PP 3d 30% | 8 | ES 1.5d 20% | PP 3d 80% | 12 | 20 | 40 | 0.65 | 0.40 | 26 | 1.6 |
| ES 3d 70% | PP 6d 30% | 8 | ES 1.5d 20% | PP 6d 80% | 12 | 20 | 40 | 0.72 | 0.49 | 25 | 1.3 |
| ES 3d 70% | PET*⁴ 1.5d 30% | 8 | ES 3d 40% | PET 1.5d 60% | 12 | 20 | 52 | 0.68 | 0.42 | 27 | 1.9 |
| ES 3d 70% | PET 3d 30% | 8 | ES 3d 40% | PET 3d 60% | 12 | 20 | 52 | 0.72 | 0.45 | 29 | 1.6 |
| ES 3d 70% | PET 6d 30% | 8 | ES 3d 40% | PT 6d 60% | 12 | 20 | 52 | 0.82 | 0.59 | 26 | 1.5 |
| ES 1.5d 100% | — | 8 | ES 3d 40% | NY*⁵ 3d 60% | 12 | 20 | 64 | 0.68 | 0.31 | 28 | 1.9 |
| ES 1.5d 100% | — | 8 g/m² | ES 3d 40% | AC*⁶ 3d 60% | 12 g/m² | 20 g/m² | 64% | 0.59 mm | 0.30 mm | 29 mm | 1.9 g |
| TP*² 3d 100% | — | 8 | TP 3d 30 | PP 2d 70% | 12 | 20 | 58 | 0.64 | 0.49 | 24 | 1.5 |
| TP 3d 100% | — | 8 | TP 3d 50% | PP 2d 50% | 12 | 20 | 70 | 0.72 | 0.53 | 23 | 1.6 |
| TP 3d 60% | PP 2d 40% | 8 | TP 3d 30% | PP 2d 70% | 12 | 20 | 66 | 0.68 | 0.44 | 28 | 1.6 |
| TP 3d 60% | PP 2d 40% | 8 | TP 3d 50% | PP 2d 50% | 12 | 20 | 54 | 0.73 | 0.59 | 23 | 1.4 |

Notes:
*¹ES: Polyethylene/polypropylene composite fiber
*²TP: Low-melting polyester/polypropylene composite fiber
*³PP: Polypropylene fiber
*⁴PET: Polyester fiber
*⁵NY: Nylon fiber
*⁶AC: Acrylic fiber

COMPARATIVE EXAMPLE 1

Sanitary napkins were produced in the same way as described in Example 1 by using, as the nonwoven covering fabric, nonwoven fabrics which were composed of various combinations of the first and second layers shown in Table 2 and whose thicknesses were outside the range of this invention. The surface flow and wet-back were measured for each of these napkins by the same methods as described in Example 1. The results are shown in Table 2.

TABLE 2

| First layer | | | Second layer | | | Basis weight | Proportion of heat-fusible fiber | Thickness 1 g/cm².hr | 5 g/cm².hr | Surface flow | Wet-back |
|---|---|---|---|---|---|---|---|---|---|---|---|
| Heat-fusible fiber | Hydrophobic fiber | Basis weight | Heat-fusible fiber | Hydrophobic fiber | Basis weight | | | | | | |
| ES 1.5d 100% | — | 8 g/m² | ES 3d 20% | PP 2d 80% | 12 g/m² | 20 g/m² | 52% | 0.30 mm | 0.17 mm | 28 mm | 2.9 g |
| ES 1.5d 100% | — | 8 | ES 3d 40% | PP 2d 60% | 12 | 20 | 64 | 0.32 | 0.15 | 31 | 3.1 |
| ES 1.5d 100% | — | 8 | ES 3d 60% | PP 2d 40% | 12 | 20 | 76 | 0.31 | 0.18 | 27 | 2.7 |
| ES 1.5d 70% | PP 2d 30% | 3 | ES 3d 40% | PP 2d 60% | 8 | 11 | 48 | 0.22 | 0.16 | 29 | 2.4 |

COMPARATIVE EXAMPLE 2

Sanitary napkins were produced in the manner as described in Example 1 by using, as the covering fabric, double-layer nonwoven fabrics composed of the first and second layers set forth in Table 3 with ratios of heat-fusible fiber to hydrophobic fiber being outside the range of this invention. The surface flow and wet-back were measured by the methods of Example 1. The results are shown in Table 3.

polyethylene/polypropylene composite fibers (ES) with a fineness of 3 deniers and a basis weight of 3 to 8 g/m$^2$.

The sanitary napkins of Comparative Example 1 showed a relatively good result in terms of surface flow, but they were quite unsatisfactory in terms of seepage and they gave an unpleasant sense of surface tackiness. Also, they were generally hard in feel as compared with the product of this invention.

The napkins of Comparative Example 2 showed sub-

TABLE 3

| First layer | | | Second layer | | | | Proportion of | Thickness | | | |
|---|---|---|---|---|---|---|---|---|---|---|---|
| Heat-fusible fiber | Hydrophobic fiber | Basis weight | Heat-fusible fiber | Hydrophobic fiber | Basis weight | Basis weight | heat-fusible fiber | 1 g/cm$^2$ .hr | 5 g/cm$^2$ .hr | Surface flow | Wet-back |
| ES 1.5d 15% | PP 2d 85% | 10 g/m$^2$ | ES 3d 30% | PP 2d 70% | 10 g/m$^2$ | 20 g/m$^2$ | 23% | 0.52 mm | 0.23 mm | 29 mm | 2.3 g |
| ES 1.5d 100% | — | 10 | ES 3d 80% | PP 2d 20% | 10 | 20 | 90 | 0.54 | 0.20 | 34 | 2.9 |
| ES 1.5d 20% | PP 2d 80% | 8 | ES 3d 50% | PP 2d 50% | 10 | 20 | 33 | 0.49 | 0.18 | 26 | 2.8 |
| ES 1.5d 60% | PP 2d 40% | 12 | ES 3d 10% | PP 2d 90% | 8 | 20 | 40 | 0.55 | 0.24 | 29 | 2.3 |
| ES 1.5d 60% | PP 2d 40% | 12 | ES 3d 90% | PP 2d 10% | 8 | 20 | 72 | 0.64 | 0.31 | 32 | 2.5 |

COMPARATIVE EXAMPLE 3

Sanitary napkins were produced in the same manner as described in Example 1 by using, as the surface layer, single-layer nonwoven fabrics composed of the fibers shown in Table 4. The surface flow and wet-back were measured in the same manner as described in Example 1. The results are shown in Table 4.

stantially the same results as those of Comparative Example 1 in terms of surface flow and seepage, but they were found defective in feel, fluffing and strength.

It was further found that in case the proportion of heat-fusible fiber is too high in either of the first and second layers, the resulting napkin has a hard feeling, whereas if the proportion of heat-fusible fiber is too small, the napkin is weak in strength and tends to be-

TABLE 4

| Hydrophilic fiber | Hydrophobic fiber | Heat-fusible fiber | | Basis weight | Thickness 1 g/cm$^2$ .hr | 5 g/cm$^2$ .hr | Surface flow | Wet-back |
|---|---|---|---|---|---|---|---|---|
| R*$^1$ 3d 100% | — | — | Binder type | 20 g/m$^2$ | 0.23 mm | 0.13 mm | 85 mm | 3.0 g |
| R- 1.5d 70% 3d 30% | — | — | " | 20 | 0.25 | 0.12 | 83 | 3.2 |
| R 1.5d 70% | PP 1.5d 30% | — | " | 20 | 0.24 | 0.15 | 92 | 3.3 |
| R 1.5d 70% | — | ES 3d 30% | — | 20 | 0.23 | 0.15 | 30 | 3.8 |
| R 1.5d 70% | — | ES 3d 30% | — | 28 | 0.38 | 0.23 | 31 | 3.6 |
| — | PP 1.5d 70% | ES 3d 30% | — | 20 | 0.23 | 0.15 | 84 | 2.8 |
| — | PP 1.5d 50% | ES 3d 50% | — | 20 | 0.25 | 0.16 | 63 | 2.7 |
| — | PP 1.5d 30% | ES 3d 70% | — | 20 | 0.23 | 0.16 | 72 | 2.6 |
| — | PP 1.5d 70% | ES 3d 30% | — | 30 | 0.31 | 0.25 | 94 | 2.2 |

Note:
*$^1$Rayon fiber

The results of Example 1 and Comparative Examples 1–3 clearly show that the sanitary napkins produced by using the nonwoven covering fabric of this invention exhibit limited blood flow on the surface and limited seepage (return) of the previously absorbed blood to the surface and thus are excellent in comfort during use.

It is especially desired from the aspects of workability and equipment cost that the first layer is entirely composed of heat-fusible fiber because a single web of carded fiber can be employed for the production of the napkin.

It is also found that, generally, good results are obtained when there is used, as the covering fabric, a two-layer nonwoven fabric in which the first layer is composed of polyethylene/polypropylene composite fiber (ES) with a fineness of 1.5 to 3 deniers and a basis weight of 7 to 9 g/m$^2$ and the second layer is composed of a mixture of polypropylene fibers (PP) with a fineness of 2 deniers and a basis weight of 5 to 11 g/m$^2$ and come fluffy and, in the worst case, it can be torn by physical friction during use. Such a proportion gives a particularly great effect to fluffing and feel of the first layer.

We claim:

1. In a sanitary napkin which is comprised of an internal absorbent medium adapted to absorb bodily discharges and a covering fabric covering at least one surface of said internal absorbent medium and adapted to contact the wearer's skin, the improvement which comprises: said covering fabric has an integrated, two-layer structure comprising an outer layer forming the surface that is adapted to contact the wearer's skin and an inner layer disposed inside of said outer layer, said covering fabric consisting essentially of from 30 to 80% by weight of heat-fusible fibers which are fusible at a temperature of from 90° to 140° C. and correspondingly from 70 to 20% by weight of hydrophobic fibers which are not fusible at a temperature below 140° C., said covering fabric having a thickness of from 0.5 to 1.2 mm under a load of 1 g/cm$^2$ and a thickness of from 0.2 to 0.6 mm under a load of 5 g/cm$^2$, the weight ratio of said heat-fusible fibers/said hydrophobic fibers in said outer layer being in the range of 50/50 to 100/0, and the weight ratio of said heat-fusible fibers/said hydrophobic fibers in said inner layer being in the range of 20/80 to 60/40.

2. The sanitary napkin according to claim 1, wherein said outer layer has a basis weight of 5 to 15 g/cm$^2$ and said inner layer has a basis weight of 8 to 25 g/cm$^2$.

3. The sanitary napkin according to claim 1, wherein said heat-fusible fibers have a fineness of 1.5 to 3 deniers and said hydrophobic fibers have a fineness of 1.5 to 6 deniers.

4. The sanitary napkin according to claim 1, wherein said heat-fusible fibers are polyethylene/polypropylene composite fibers and said hydrophobic fibers are polypropylene fibers or polyester fibers.

5. The sanitary napkin according to claim 1, wherein said outer layer is composed of polyethylene/polypropylene composite fibers of 1.5 to 3 deniers and having a basis weight of 7 to 9 g/m$^2$, and said inner layer is composed of a mixture comprising 3 to 8 g/m$^2$ of polyethylene/polypropylene composite fibers of 3 deniers and 5 to 11 g/m$^2$ of polypropylene fibers of 2 deniers.

6. The sanitary napkin according to claim 2, in which said outer layer has a lower basis weight and contains a higher proportion of heat-fusible fibers than said inner layer.

7. In a sanitary napkin which is comprised of an internal absorbent medium adapted to absorb bodily discharges and a covering fabric covering at least one surface of said internal absorbent medium and adapted to contact the wearer's skin, the improvement which comprises: said covering fabric has an integrated, two-layer structure comprising an outer layer forming the surface that is adapted to contact the wearer's skin and an inner layer disposed inside of said outer layer, said covering fabric consisting essentially of from 30 to 80% by weight of heat-fusible fibers which are fusible at a temperature of from 90° to 140° C., said heat-fusible fibers being selected from the group consisting of polyester/polypropylene composite fibers and polyethylene/propylene composite fibers, and correspondingly from 70 to 20% by weight of hydrophobic fibers which are not fusible at a temperature below 140° C., said hydrophobic fibers being selected from the group consisting of polyproylene fibers, polyester fibers, nylon fibers and acrylic fibers, said inner and outer layers being adhered to each other by heat-bonding of said heat-fusible fibers, said covering fabric having a thickness of from 0.5 to 1.2 mm under a load of 1 g/cm$^2$ and a thickness of from 0.2 to 0.6 mm under a load of 5 g/cm$^2$, the weight ratio of said heat-fusible fibers/said hydrophobic fibers in said outer layer being in the range of 50/50 to 100/0, and the weight ratio of said heat-fusible fibers/said hydrophobic fibers in said inner layer being in the range of 20/80 to 60/40, said outer layer containing a higher proportion of heat-fusible fibers than said inner layer, and said outer layer has a basis weight in the range of 5 to 15 g/cm$^2$ and said inner layer has a basis weight in the range of 8 to 25 g/cm$^2$, the basis weight of said outer layer being lower than the basis weight of said inner layer.

8. A sanitary napkin according to claim 7, wherein said heat-fusible fibers have a fineness of 1.5 to 3 deniers and said hydrophobic fibers have a fineness of 1.5 to 6 deniers.

9. A sanitary napkin according to claim 7, wherein said absorbent medium comprises a bottom layer of a polymer absorbent, an absorbent paper layer superposed on said polymer absorbent layer, a fluff pulp layer superposed on said absorbent paper layer, and a top layer of a fiber selected from the group consisting of rayon staple fiber and cotton fiber, said top layer being superposed on said fluff pulp layer, and said sanitary napkin further comprises a waterproof film which covers the bottom and sides of said absorbent medium.

10. A sanitary napkin according to claim 9, wherein said covering fabric entirely covers said absorbent medium and said waterproof film.

* * * * *